United States Patent [19]

Hanson et al.

[11] 4,402,307

[45] Sep. 6, 1983

[54] BALLOON CATHETER WITH ROTATABLE ENERGY STORING SUPPORT MEMBER

[75] Inventors: Bruce L. Hanson, Wayne, N.J.; Sidney Wolvek, Brooklyn, N.Y.

[73] Assignee: Datascope Corp., Oakland, N.J.

[21] Appl. No.: 202,868

[22] Filed: Oct. 31, 1980

[51] Int. Cl.³ .................... A61B 19/00; A61M 29/02
[52] U.S. Cl. .................................. 128/1 D; 128/344; 604/95
[58] Field of Search ....... 128/1 D, 344, 325, 348–350, 128/DIG. 9; 604/95–103

[56] References Cited

U.S. PATENT DOCUMENTS

| | | | |
|---|---|---|---|
| 3,789,841 | 2/1974 | Antoshkiw | 128/DIG. 9 |
| 3,978,863 | 9/1976 | Fettel | 128/348 |
| 4,261,339 | 4/1981 | Hanson et al. | 128/1 D |
| 4,271,839 | 6/1981 | Fogarty et al. | 128/344 |
| 4,292,974 | 10/1981 | Fogarty et al. | 128/344 |
| 4,299,226 | 11/1981 | Banka | 128/344 |

FOREIGN PATENT DOCUMENTS 439636 4/1912 France .................. 128/344

Primary Examiner—Dalton L. Truluck
Attorney, Agent, or Firm—Darby & Darby

[57] ABSTRACT

An intra-aortic balloon adapted to be percutaneously inserted into a blood vessel in which the balloon and its support member are twisted as the balloon envelope is wrapped around its support member before insertion into the vessel to reduce the diameter of the balloon envelope. The support member is twisted as the balloon is wrapped, thereby storing energy which, urges the unwrapping of the balloon in the vessel. In one embodiment, the support member is hollow to permit a guide wire to pass there-through so that placement of the balloon within the human body may be done with greater precision and the hollow support member permits the injection of a radiopaque fluid so that the balloon can be viewed within the vessel, thereby assisting in the placement of the balloon. In another embodiment, a solid energy storage support member with a highly flexible distal portion provides an intra-aortic balloon of enhanced pliability.

24 Claims, 7 Drawing Figures

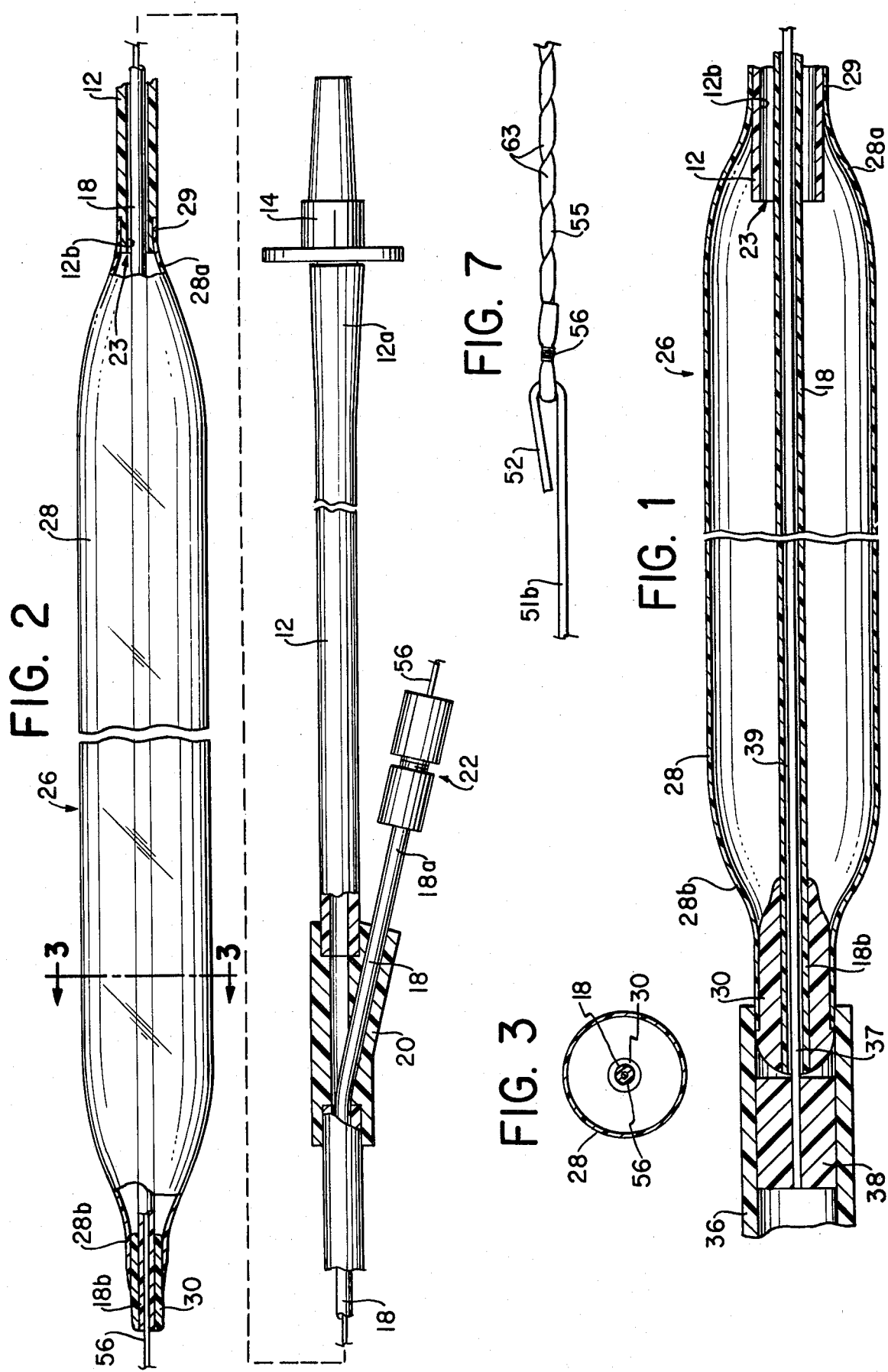

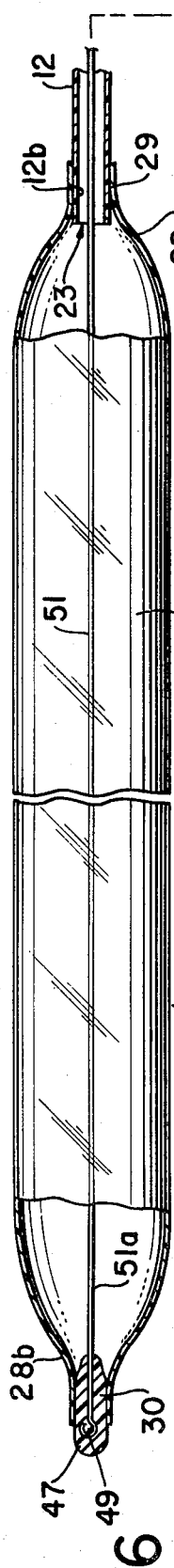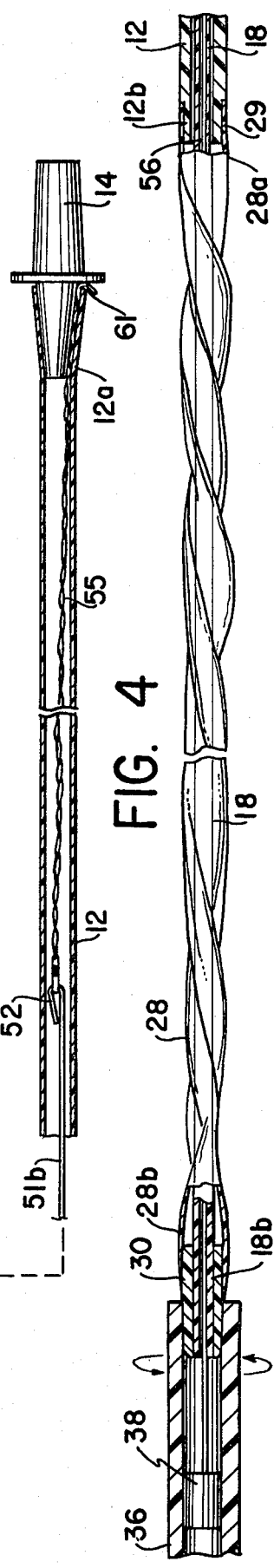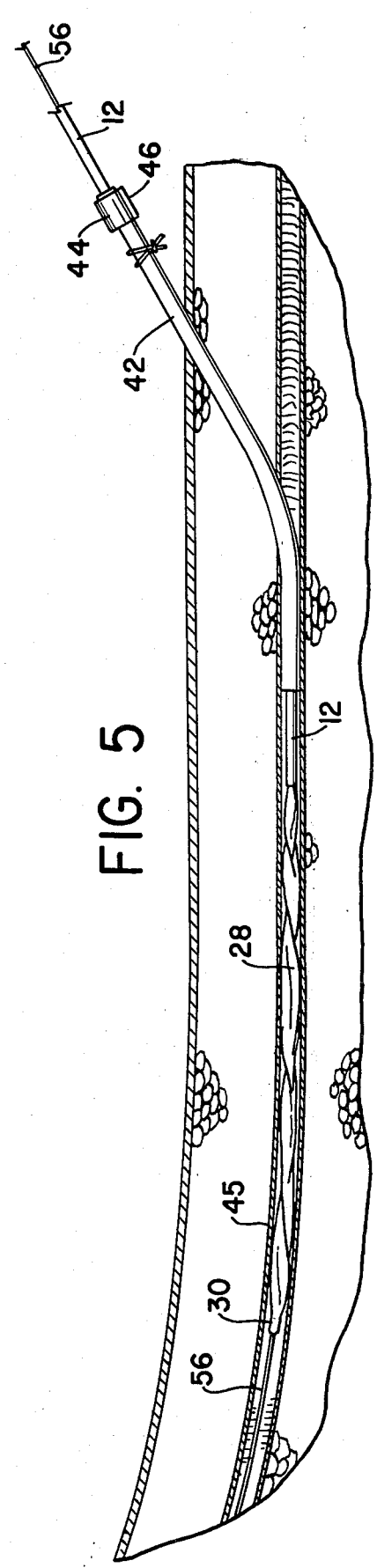

BALLOON CATHETER WITH ROTATABLE ENERGY STORING SUPPORT MEMBER

Intra-aortic balloons (IAB) are well known. Typical balloons are shown in U.S. Pat. Nos. 3,504,662, granted Apr. 7, 1970 to Jones, 3,692,018 granted September 1972 to Goetz, et al., and 3,939,820 granted Feb. 24, 1976 to Grayzel. They include an inflatable envelope mounted on a support member attached to the catheter. The envelope is alternatively inflated and deflated through the catheter to achieve blood pumping action. The intra-aortic balloons of these patents are typical of many which are inserted into the arteries of the human body by vascular surgical procedures in which the artery is exposed, opened, and finally sutured closed upon the removal of the balloon catheter.

In our copending application Ser. No. 883,513, filed March 6, 1978, now U.S. Pat. No. 4,261,339 granted Apr. 14, 1981 and which is assigned to the same assignee, an IAB is shown in which the balloon envelope is wrapped around its rotatable support member to reduce its external diameter. This permits a simpler vascular procedure, thereby making it easier to insert the balloon into the aorta. This reduces the operating time.

In our copending application Ser. No. 86,150, filed Oct. 18, 1979, and which is assigned to the same assignee, a system is disclosed for inserting the IAB through the skin, i.e. percutaneously, into an artery of a patient. The system of that patent can utilize the balloon of our U.S. Pat. No. 4,261,339. A system and IAB for percutaneous insertion is desirable since the involved vascular surgical procedure, which can only be performed by a limited number of specialists, is eliminated. The percutaneous insertion technique is within the skill of a larger number of surgeons and other medical personnel.

The balloon catheter described in our U.S. Pat. No. 4,261,339, having the balloon envelope wrapped around the support member, when inserted by the system described in our copending application 86,150 reduces the time and severity of insertion surgery. The balloon envelope depends on its own elastomeric nature and the inflating gas pressure to achieve unwrapping.

The present invention is directed to an improved wrappable balloon which can be percutaneously inserted and in which unwrapping of the envelope when in the artery is actively assisted by the balloon support member. In accordance with the invention, the envelope of an IAB is attached to a catheter through which a suitable fluid is supplied to inflate and deflate the envelope. The envelope is wrappable around and twistable with its support member. The support member extends for a distance back into the catheter and has a part fixed within the catheter so that as the balloon envelope is wrapped, the support member twists and stores energy. After the balloon is inserted into the artery and the envelope is to be unwrapped, the stored energy in the support member is released, and urges unwrapping of the balloon envelope.

In a preferred embodiment of the invention, the support member is hollow and one of its ends is attached within the catheter. The hollow support member for the balloon envelope also permits a guide wire, which has been previously introduced into the artery, to be inserted therethrough from outside of the body. The guide wire aids in guiding the IAB to the desired location within the artery. The balloon catheter can be viewed as it is so guided.

In another embodiment of the invention the twistable support member is a solid, rod-like, member. The member is fixed within the balloon tip at one end and is affixed at its other end to a band of suitable elastomeric material, such as rubber or latex, which extends into and is connected to the catheter to achieve the capacity for the energy storage required for assisting the unwrapping of the envelope.

It is therefore an object of the present invention to provide a balloon catheter for percutaneous insertion into a blood vessel or body passage of a patient.

Another object is to provide an improved balloon catheter which is mounted to a support member which twists to store energy as the envelope is wrapped, the stored energy later being available to urge the unwrapping of the envelope in the artery.

A further object is to provide an improved IAB for percutaneous insertion by which the balloon can be guided to a desired place in a vessel of a patient by moving it along a guide wire.

An additional object is to provide a support member that serves as a conduit for radiopaque fluid to enable the person inserting the balloon to visualize the artery in order to precisely locate the IAB within the human body.

Yet another object is to provide a means for wrapping the balloon envelope about its hollow twistable support member while retaining a straight inner lumen of said support member.

Another object is to provide an improved IAB which is mounted to a solid support member which stores energy as the balloon envelope is wrapped and which will, at the same time, provide an extremely flexible distal portion to the IAB.

Other objects and advantages of the present invention will become more apparent upon reference to the following specification and annexed drawings in which:

FIG. 1 is an overall view of the IAB and a wrapping device in the form of a stylet for wrapping the envelope and twisting the member;

FIG. 2 is an enlarged view of the envelope, support member, and catheter, shown extended and partially in section;

FIG. 3 is a cross-section of the envelope and support member taken along lines 3—3 of FIG. 2;

FIG. 4 is a longitudinal plan view, partly in cross-section, showing the wrapping of the balloon by a wrapping stylet and the twisting of the support member;

FIG. 5 if a view, partly in cross-section, showing the insertion of the balloon into an artery;

FIG. 6 is an enlarged view of an alternate embodiment of the IAB shown extended and partially in section; and FIG. 7 is a detail of FIG. 6 at the junction of the proximal end of the solid support.

Referring to drawings, and particularly to FIGS. 1-3, the IAB includes as its main components a catheter 12 of a suitable elastomeric material, such as polyurethane, of extended length, for example, about 36 inches. One (proximal) end 12a of the catheter which is to be located external of the body, has a Luer type fitting 14 fastened thereto to accept a valve (not shown), or to make direct connection with a device which can apply either air or some other fluid under pressure through the catheter and can withdraw the same.

A hollow support member 18, also of a suitable elastomeric material such as polyurethane, passes through the length of the catheter 12 starting from a "Y" fitting 20 near the proximal end 12a of the catheter where it is fastened, such as by an adhesive or heat sealing or welding. The proximal end 18a of the support member 18 which exits from the catheter "Y" fitting 20 has a Luer fitting 22 thereon to permit insertion of a guide wire 56, to be described below.

A balloon 26 includes an envelope 28 of a suitable plastic material, for example, polyurethane, which can be inflated by the fluid applied through the catheter and deflated by withdrawing the fluid through the catheter. One end 28a (hereinafter called the proximal end) of envelope 28 is attached fluid-tightly, for example, by cementing, heat sealing, etc., in the area 29 around the distal end 12b of the catheter 12 which is to be inserted into the body and is remote from the Luer fitting 14. The other end 28b of the envelope (hereinafter called the distal end) is fastened in a fluid-tight manner, also by a cement or a heat sealing, to the outer surface of a tip 30, of a suitable plastic material and which is preferably radiopaque or contains a radiopaque substance such as barium. The (distal) end 18b of the support member 18 remote from fitting 22 is attached to the inside of the tip 30 such as by cementing, molding, etc.

Thus, the balloon envelope 28 is fastened in a fluid tight manner at its proximal end 28a to the catheter end 12b and at its distal end 28b to the tip 30. The support member 18 extends the length of envelope 28 and into the catheter. While the support member distal end 18b is attached to the tip 30 and the tip 30 is attached to the distal end 28b of the envelope, the support member near the envelope proximal end 28a is not attached thereto but passes through the catheter 12 along most of its length until the the exit and attachment point within "Y" fitting 20. There is a communication space 23 between the support member 18 and the catheter 12 since the outer diameter of support member 18 is less than the diameter of the catheter opening. This is shown best at the right hand side of FIG. 1 and FIG. 2. It is through this space 23 that the fluid is provided to and withdrawn from the envelope. As shown, the catheter distal end extends for only a short distance into, or effectively terminates at, the proximal end 28a of the envelope. Thus, fluid is injected into the proximal end of the envelope.

In a typical case, the catheter has an outside diameter of about 0.170 inches and an inner diameter of about 0.130 inches. The support member 18 has an outer diameter of about 0.070 inches and an inner diameter of about 0.035 inches.

The balloon envelope 28 is of a suitable plastic material, such as polyurethane having a thickness in the range of from about 0.003 inches to about 0.005 inches. The envelope 28 is illustratively shown as being of uniform diameter, except for the tapered ends, along its length of from about 8 to 10 inches although other lengths can be used. Other shapes, for example a tapered shape or multi-chamber, and length can be utilized for the envelope. The length of the support member 18 within the envelope corresponds to the length of the envelope. The preferred envelope material is one which will expand and collapse but which is not elastic. It should be understood, however, that the envelope may also be of an elastic or semi-elastic material.

The tubular support member 18 has sufficient resiliency and memory to support the balloon envelope 26. At the same time, it is thin enough to permit the balloon to pass through the comparatively narrow opening of a small blood vessel, body passage, or vascular sheath to be described below. When a negative pressure is applied to the interior of the balloon envelope 18 via catheter 12, the balloon envelope collapses. Conversely, application of pressure to the interior of the envelope 28 via the catheter 18 causes it to inflate.

Another component of the system is a wrapping stylet 36 (FIG. 1 and 4). This is a piece of tubular soft plastic material of a suitable length, for example about 6 to 8 inches. The wrapping stylet has a plug 38 fastened near one end recessed to a depth about equal to or somewhat less than the exposed portion of the balloon tip 30. The wrapping stylet's soft plastic material is sized to prvide a tight fit over the balloon tip 30 as that rotation of the stylet will rotate the envelope 38 and the support member 18.

A wrapping stylet wire 37, constructed of an appropriate stiff material such as stainless steel is firmly affixed within the wrapping plug 38 and loosely occupies the inner lumen 39 of the support member 18 when the wrapping stylet is in position over the balloon tip 30. The stylet wire preferably occupies the entire length of that portion of the support member that resides within the balloon membrane 28, terminating within the catheter in the vicinity of balloon/catheter junction 29. Wire 37 within the lumen of the hollow support member insures that the support member will twist about its own axis during balloon wrapping and that it will remain longitudinally straight, thus insuring a small diameter wrapped balloon and a straight inner lumen to allow the easy passage of a guide wire therethrough.

A three-way stopcock (not shown) is attached to the Luer fitting 15 at the proximal end 12a of the catheter 12. The stopcock is adjusted to vent the balloon to atmosphere.

The balloon envelope 28 is wrapped around support member 18 (see FIG. 4) by placing the end of the wrapping stylet 36 over the tip 30 of the support member at the distal end of the envelope. The tip 30 fits within the recess at the end of the wrapping stylet tube so that a firm grip is made on the tip 30 and the wire 37 extends within the support member lumen. The wrapping stylet 36 is rotated by the doctor or his assistant. Since the support member is fastened to tip 30 and to the catheter 12 at point 20 near the inlet fitting 14, it is also rotated, or twisted, as the wrapping stylet is rotated. Stylet wire 37 within support lumen 39 insures the straight axial twisting of the support member.

The rotation of the support member 18 stores energy along its length. During the rotation of wrapping stylet 36, the balloon envelope, having its proximal end 28a affixed to the proximal end 12b of the catheter, is wrapped around the support member in a more or less helical manner. This is shown by FIG. 4. This reduces the diameter of the balloon. Suction (negative) pressure is applied through the catheter to the balloon envelope chamber by means of the stopcock and a syringe or other suitable device of appropriate size to keep the envelope collapsed after the wrapping and also during advancement into the body. Application of suction pressure is continued after the wrapping to hold the balloon collapsed and wrapped thereby also holding the support member twisted with the energy stored.

It is preferred that the IAB be inserted percutaneously, although it can be inserted using a vascular cutdown procedure. Percutaneous insertion is accomplished with the use of a sheath/dilator/safety guide apparatus employing a system such as described in our copending application Ser. No. 86,150. In this system, a hollow needle (not shown) is first used to puncture the skin and provide communication to the artery. A guide wire is then inserted into the artery via the hollow needle which is then withdrawn from about the wire and discarded. A dilator with a through bore to accommodate the guide wire and fitted with a thin sheath on its outer circumference is then passed over the wire into the artery in order to enlarge the puncture. The dilator is then withdrawn from about the guide wire and from within the sheath leaving the sheath in place as shown as 42 in FIG. 5. The sheath provides an entrance passage into the artery from external of the patient's body.

Referring to FIG. 5, with sheath 42 in place within the patient's artery 45, the guide wire extends through the sheath from within the artery with a length of the wire being free outside of the body. Bleeding can be controlled at this time by pinching that portion of the sheath 42 extending from the body tissue.

The end of guide wire 56 extending outside of the body is next threaded through the tip 30 of the IAB. The IAB with the envelope wrapped and the attached catheter are advanced along the guide wire 56 until the free end of the guide wire extending outside of the body has passed along the entire length of the support member and out of the support member fitting 22. The overall length of the guide wire is selected such that after insertion into the body it will extend the length of the support member and exit from fitting 22 when the balloon tip 30 is fairly close to the end of the sheath 42 which is extending outside of the body.

The IAB, with the envelope wrapped as previously described and shown in FIG. 4, is then advanced into the sheath 42. The leakage of the patient's blood into the sheath lubricates its interior wall making the advancement of the IAB through the sheath and into the artery much easier. It should be understood that flow of the blood through the sheath before the IAB is inserted is controlled by clamping the sheath. The advancement continues until the balloon passes out of the sheath into the artery leaving the catheter in the sheath. The balloon is further advanced over the guide wire in the aorta until the desired position within the patient's body has been reached. This position can be confirmed radiographically since the balloon tip 30 is radiopaque. When the balloon is at the desired position, the guide wire is withdrawn.

In another method, the guide wire 56 is removed from the puncture site with the dilator leaving only the sheath in place. A guide wire may then be inserted directly into the wrapped balloon after the removal of the wrapping means 36 prior to the introduction of the balloon into the sheath 42. That portion of the guide wire extending beyond the fitting 22 may be used to regulate the length of wire protruding beyond the balloon tip 30. The balloon may then be passed directly into sheath 42 and the length of the guide wire protruding beyond the balloon tip may be regulated from the fitting end 22 to provide efficient guidance.

It should be understood that the new IAB does not depend on the guide wire to achieve insertion and introduction. The IAB may be inserted directly through a sheath while in its wrapped condition. The guide wire adds to the safety and convenience of the procedure.

The hollow lumen support member 18 may be used for the injection of radiopaque dye, for instance, for the radiographic examination of the artery, or it may be used to obtain blood sample from various portions of the body or it may be used to acquire blood pressures by the connection of a pressure transducer to the support member fitting 22. It is also to be understood that "Y" fitting 20 may contain a plurality of ports for the simultaneous acquisition of the various data from the within human body.

When the balloon is at the desired location within the artery, the envelope is unwrapped. This is accomplished by adjusting the three-way stopcock which has been attached to Luer fitting 14 so that the low pressure inside the balloon envelope is relieved to atmospheric air pressure. This causes the support member 18 to be effectively released and it untwists by the action of its stored energy. The untwisting of the support member 18 causes it to urge the unwrapping of the balloon envelope relative to the catheter. The inflation of the envelope by positive pressure will fully unwrap the envelope if it has not previously been fully unwrapped.

In another embodiment, as seen in FIG. 6, a solid support member 51 is used instead of hollow support member 18. Solid support member 51 may be of a suitable metal, such as stainless steel, or of a suitable plastic material such as high molecular weight polyethylene or of nylon, having a torsional stiffness appropriate to transmitting the wrapping torsion from its distal end 51a to is proximal end 51b.

Distal end 51a of support member 51 terminates in a hook 49 or other suitable enlarged section which is molded directly into a tip 47 of the IAB which tip may be of a suitable thermoplastic material such as polyurethane. The proximal end 51b terminates in a hook-like configuration 52 located within the catheter 12 to which is attached an elastic band 55. The elastic band may be attached by a wrapping 56 as is shown in FIG. 7, or by cementing or other appropriate means. The proximal end of elastic band 55 is secured for instance at point 61 between the inner wall of catheter 12 and the outer surface of Luer fitting 14 while the elastic band is under a slight tension. Surplus elastic band material 61 may be trimmed away, as indicated, after assembly.

The envelope 28 is wrapped by the stylet in the manner previously described. The rotational energy developed by the rotation of tip 47 during the wrapping of balloon envelope 28 is transmitted by solid support member 51 to the taut elastic band 55, where it is stored in the form of twist 63 in the elastic band. The twist of the band is held when the envelope is subjected to reduced pressure. Since the support member 51 is solid, no guide wire can be used and the IAB is advanced directly into the artery through the sheath. When the balloon is at the desired location within the artery and the vacuum within the balloon is released, the stored torsional energy in elastic band 55 is imparted to support member 51 which then imparts a rotation to tip 47 urging the balloon to unwrap within the body.

The distal portion 53 of solid support 51 may be treated, for example by annealing or by an appropriate configurational modification, to be more flexible longitudinally than the main portion 51 while at the same time, retaining its ability to transmit torsion. This results in a balloon catheter having an extremely flexible distal portion, thereby enhancing its safety and aiding its ability to follow a tortuuous pathway within the passages of the human body.

While the balloon catheter and system has been described with respect to intra-aortic balloon pumping, it should be understood that it can be used in many other applications where balloon catheters are commonly used. For instance, it may be used to occlude the aorta during aortic repair or resection. Here, a fluid such as normal saline solution may be used to inflate the envelope rather than the air or gas that is supplied to the envelope during intra-aortic balloon pumping.

As should be apparent, the hollow support member 18 for the envelope provides several advantages. First, it permits passage of a guide wire through the balloon. This makes the balloon easier to guide in the passages and blood vessels of the body. Secondly, it provides a passage through which fluids, such as radiopaque dye can be inserted into the artery ahead of the IAB system. These two advantages are present in addition to the energy storage function which is utilized when the balloon is wrapped and are present even without the wrapping. The energy storage function also can be achieved by using a solid support member, as in the alternative embodiment. In this case, however, the first two functions would not be obtained.

What is claimed:

1. An intra-aortic balloon device for the body of a subject comprising:
   an elongated tubular catheter having a distal end adapted to be inserted into the body and a proximal end,
   an inflatable and deflatable envelope having its distal end sealed and its proximal end attached to the distal end of said catheter, said catheter adapted for supplying fluid therethrough to inflate and deflate said envelope,
   an elongated member having a distal first portion extending within the envelope to form a support therefor and a second portion extending within said catheter, the distal end of said envelope being attached to the distal end of said elongated member,
   means for attaching the second portion of said elongated member to said catheter, at least part of said elongated member being of a material which is twisted relative to its longitudinal axis to store energy as said envelope is rotated to wrap it relative to said catheter and said elongated member is rotated between the distal end of said envelope and its part of the second portion attached to the catheter, said energy storage part of said elongated member having a retentive memory to untwist and to tend to restore to its original shape by releasing its energy stored during twisting to assist in unwrapping the envelope.

2. A device as in claim 1 further comprising means for rotating said elongated member, the rotation of said elongated member wrapping said envelope around said first portion of said elongated member with the envelope twisting about its proximal end which is attached to said catheter.

3. A device as in claim 2 wherein said means for rotating said elongated member comprises a tip piece at said distal end of said envelope to which the distal end of the first portion of said elongated member is connected.

4. A device as in claim 3 wherein said means for rotating said elongated member further comprises a member for engaging said tip piece.

5. A device as in claim 1 further comprising means for applying fluid to the interior of said envelope through said catheter, applying negative pressure to said envelope holding the envelope in the wrapped condition and said elongated member energy storage part in the twisted condition, the release of said elongated member permitting it to return to its relaxed state and thereby assist in the unwrapping of the envelope.

6. A device as in claim 5 wherein said catheter has an opening at its distal end, through which the fluid is applied to and withdrawn from said envelope, said catheter distal end terminating at the proximal end of the envelope.

7. A device as in claim 1 wherein the entire length of said elongated member comprises the part for storing the energy.

8. A device as in either claim 1 or 7 where said elongated member is hollow along its length and has an opening for communicating with an environment external to the envelope at each end thereof.

9. A device as in claim 8 wherein said catheter is elongated and is formed with an exit port at its proximal end, said second portion of said elongated member extending into said catheter passing through said catheter exit port and exiting from said catheter, said attaching means for said second portion of said elongated member fixedly attaching said second portion to said catheter at said exit port.

10. A device as in claim 9 further comprising a guide means adapted to pass through said hollow elongated member and over which said device can be moved.

11. A device as in claim 10 further comprising a sheath for insertion through a percutaneous opening of the body into an artery, said guide means adapted to pass into the artery through said sheath and said balloon device passing over said guide means and through said sheath into the artery.

12. A device as in claim 11 further comprising means for applying fluid to the interior of said envelope through said catheter, applying negative pressure to said envelope holding the envelope in the wrapped condition and said elongated member in the twisted condition, the release of said elongated member permitting it to untwist and assist in the unwrapping of the envelope.

13. A device as in claim 1 further comprising means for rotating said elongated member, the rotation of said elongated member wrapping said envelope around said first portion of said elongated member with the envelope twisting about its said proximal end which is fastened to said catheter.

14. A device as in claim 1 wherein said first portion of said elongated member within said envelope is hollow along at least a portion of its length.

15. A device as in either claim 13 or 14 wherein said means for rotating said elongated member comprises means for engaging and rotating the distal end of said envelope, said engaging and rotating means including an elongated piece extending into the hollow first portion of said elongated member for at least a portion of the length of said envelope to maintain said envelope portion generally straight during rotation of said elongated member.

16. A device as in claim 1 wherein said twistable energy storage part of said elongated member is within said catheter and comprises an elastic member.

17. A device as in claim 16 wherein said elastic member is a stretchable band which is held within said catheter.

18. A device as in claim 1 wherein said first portion of said elongated member within said envelope is solid.

19. A device as in claim 18 wherein said twistable energy storage part of said elongated member is within said catheter and comprises an elastic member.

20. A device as in claim 19 wherein said elastic member is a stretchable band which is held within said catheter.

21. A device as in claim 20 further comprising means for connecting one end of said band to the proximal end of said solid first portion of said elongated member.

22. A device as in claim 21 wherein said connecting means is located in said catheter.

23. A device as in either claim 1 or 17 wherein said first portion of said elongated member within said envelope has variable flexibility between its distal end and its proximal end.

24. A device as in claim 23 wherein said first portion of said elongated member is more flexible at its distal end than at its proximal end.

* * * * *